United States Patent [19]

Ohsawa et al.

[11] Patent Number: 5,834,451
[45] Date of Patent: Nov. 10, 1998

[54] REMEDY FOR MYOTONIC DYSTROPHY

[75] Inventors: Nakaaki Ohsawa; Masakazu Sugino, both of Osaka; Tomio Endo, Nishinomiya, all of Japan

[73] Assignee: Kanebo Ltd., Tokyo, Japan

[21] Appl. No.: 776,888

[22] PCT Filed: Aug. 7, 1995

[86] PCT No.: PCT/JP95/01561

§ 371 Date: Apr. 15, 1997

§ 102(e) Date: Apr. 15, 1997

[87] PCT Pub. No.: WO96/04917

PCT Pub. Date: Feb. 22, 1996

[30] Foreign Application Priority Data

Aug. 8, 1994 [JP] Japan .................................. 6-205939

[51] Int. Cl.$^6$ .................................................. A61K 31/56
[52] U.S. Cl. ............................ 514/177; 514/178; 514/179
[58] Field of Search ........................................ 514/177, 178, 514/179

[56] References Cited

U.S. PATENT DOCUMENTS 4,005,200  1/1977  Utsumi et al. ........................ 514/177

OTHER PUBLICATIONS

Carter, J.N. and K.S. Steinbeck, "Reduced Adrenal Androgens in Patients with Myotonic Dystrophy", *Journal of Clinical Endocrinology and Metabolism*, vol. 60 No. 3, Mar. 1985, pp. 611–614.

*Primary Examiner*—Jerome D. Goldberg
*Attorney, Agent, or Firm*—Pollock, Vande Sande & Priddy

[57] ABSTRACT

A remedy for myotonic dystrophy, containing dehydroepiandrosterone sulfate or a pharmacologically acceptable salt thereof, being efficacious for myotonia, adynamia and amyotrophy, and having a high safety.

16 Claims, No Drawings

REMEDY FOR MYOTONIC DYSTROPHY

This application is a 371 of PCT/JP95/01561 filed Aug. 7, 1995.

TECHNICAL FIELD

The present invention relates to a remedy efficacious for symptomatic improvement in myotonic dystrophy and various other diseases manifesting myotonia.

BACKGROUND ART

Myotonic dystrophy (hereinafter referred to sometimes as MyD) is an autosomal-dominant hereditary disease caused by abnormalities of the long arm of chromosome 19 and its morbidity is said to be 4 to 5 in 100,000. MyD is a degenerative disease, the cardinal symptoms of which are muscular atrophy and decreased muscle strength dominantly found in muscles of the face and neck and in distal muscles of the limbs, and appearance of repetitive muscle cell membrane action potentials in skeletal muscles on contraction and consequent delays in relaxation (myotonia), and which is complicated by multiple organ disorders.

There is no causal therapy available for MyD and in clinical practice today symptomatic therapies are being attempted for said myotonia and complicating organ disorders.

Thus, medicines such as procainamide, diphenylhydantoin, taurine are administered for the treatment of myotonia.

However, the above-mentioned medicines have the drawback that their administration results in adverse reactions such as induction and aggravation of the conduction disorders of the heart as complications of MyD, gastrointestinal disorders, central nervous system symptoms, etc. and that the therapeutic results are not necessarily reproducible.

In MyD, not only the above-mentioned myotonia but also decreased muscle strength and muscular atrophy, which can be the most serious detracting factor in the patient's activity of daily living, are encountered but no established therapy for such disorders is available as of the present time.

SUMMARY OF THE INVENTION

In view of the above state of the art, the present invention has for its object to provide a remedy which is very efficacious for said myotonia, decreased muscle strength, and muscular atrophy and highly safe to use.

The present invention resides essentially in utilizing dehydroepiandrosterone sulfate or a pharmacologically acceptable salt thereof in the treatment of myotonic dystrophy and myotonia.

DETAILED DISCLOSURE OF THE INVENTION

The present invention is now described in detail.

Dehydroepiandrosterone sulfate (hereinafter referred to briefly as DHEA-S) and dehydroepiandrosterone (briefly, DHEA) are adrenocortical androgens produced and released from the human adrenal cortex. They are $C_{19}$ steroid hormones which are intrinsic to Primates. DHEA-S is readily converted to DHEA in vivo. In view of its metabolic pathways, it can be theoretically further transformed into testosterone and estrogen but the actual conversion rates are extremely low. The physiological activities of DHEA-S and DHEA have been little elucidated and although it has been found that DHEA has androgen-like activity, its activity as a male hormone is weak.

Research by the inventors of the present invention revealed that blood DHEA and DHEA-S levels are significantly lower in MyD patients than in healthy individuals in the same decade of life and that, therefore, DHEA and DHEA-S could be used as remedies for MyD.

DHEA-S in accordance with the present invention, has the structure (1) shown below, as is disclosed in Japanese Kokoku Publication Sho-55-27884.

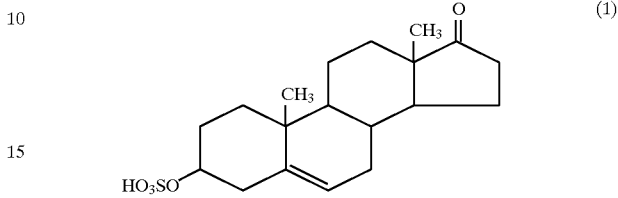

In Japan, dehydroepiandrosterone sulfate sodium salt (hereinafter briefly referred to as DHEA-S.Na) according to the present invention, has been on the market since 1984 as a remedy for insufficient maturity of the cervical canal in the third pregnancy trimester, which is to be used as the main ingredient in the trademark Mylis Injection.

Therefore, the above-mentioned DHEA-S or a pharmacologically acceptable salt thereof is a per se known substance. However, the use thereof as a remedy for MyD has never been suggested.

DHEA-S is generally used in the form of sodium salt. It can also be used for parenteral administration in the form of solutions of other water-soluble salts, such as the potassium and ammonium salts. The free sulfate and insoluble salts such as the calcium, magnesium and aluminum salts can be used for oral administration in the form of tablets, capsules and so forth. Parenteral administration for intravenous injection or intramuscular injection as well as oral administration are preferred among others.

One or more of the solid, semisolid or liquid diluents, fillers and other pharmaceutical additives are used as the carriers in an amount of, for example, 0.1% to 99.5%, preferably 0.5% to 90%. The remedy for myotonic dystrophy according to the present invention can be safely administered either orally or parenterally. The parenteral dosage forms are applied, for example, by local administration into a tissue, subcutaneous administration, intramuscular administration, intraarterial or intravenous administration, or rectal administration. Preparations suited for these routes of administration can be produced using the per se known conventional means and techniques. The dose as the remedy for myotonic dystrophy is desirably determined according to the patient's age and weight, the route of administration, the kind and the severity of the disease, and other factors. Generally, however, in the case of administration to humans, the usual oral dose for adults as expressed on the active ingredient basis is 10 to 2,000 mg/day, preferably 50 to 1,000 mg/day. For parenteral administration, doses of 10 to 1,000 mg/day, preferably 50 to 500 mg/day, are generally recommended although the proper dose may vary greatly according to the administration route employed. In some cases, smaller doses will be sufficient or larger doses may be required. Administration in two to four divided doses per day is also possible.

Oral administration can be carried out using the unit dose of a solid or liquid dosage form such as powdered drug, powder, granules, tablets, capsules, syrups, elixirs or suspensions.

The powdered drug is prepared by finely dividing the active ingredient to an appropriate size. The powder dosage form are produced by finely dividing the active ingredient to an appropriate size and admixing the same with a pharmaceutical carrier finely divided in the same manner, for example edible carbohydrates such as starch and mannitol or other excipients. When necessary, flavorings, preservatives, dispersing agents, coloring agents, perfumes and other additives may be admixed.

Capsules are produced by filling capsule shells, for example gelatin capsule shells, with the powdered drug or powder prepared in the above manner or with granules prepared in advance. Before filling, a lubricant or flowability improver, such as colloidal silica, talc, magnesium stearate, calcium stearate or solid polyethylene glycol, may be admixed as desired. The efficacy of the drug taken in a capsule form can be improved by adding a disintegrant or solubilizing agent such as carboxymethylcellulose, carboxymethylcellulose calcium, low-substituted hydroxypropylcellulose, croscarmellose sodium, carboxystarch sodium, calcium carbonate or sodium carbonate.

Soft capsules can be made by suspending and dispersing the active ingredient in finely divided form in a vegetable oil, polyethylene glycol, glycerol, a surfactant or the like and enwrapping the suspension with a gelatin sheet.

Granules can be prepared by adding, as necessary, a binder (e.g. carboxymethylcellulose sodium, hydroxypropylcellulose, methylcellulose, hydroxypropylmethylcellulose, gelatin, polyvinylpyrrolidone, polyvinyl alcohol, etc.) and a wetting agent (e.g. syrup, starch paste, gum arabic, cellulose solution, macromolecular substance solution, etc.) to a mixture of the active ingredient in powder form and the above-mentioned excipient and disintegrant, and kneading the resulting mixture, followed by forcedly passing the same through a sieve. Instead of such manner of granulation of the powder, granules can also be made by submitting the powder to a tableting machine and grinding the thus-obtained slugs incomplete in form and shape. A dissolution retarder (e.g. paraffin, wax, hardened castor oil, etc.), a reabsorption agent (e.g. quaternary salt etc.), an adsorbent (e.g. bentonite, kaolin, dicalcium phosphate, etc.) and/or the like may optionally be admixed beforehand.

Tablets can be prepared by adding, to the thus-produced granules, a lubricant, for example stearic acid, a stearic acid salt, talc or mineral oil, and tableting the resulting mixture. The thus-produced plain tablets may be further provided with a film or sugar coating.

The active ingredient may also be admixed with a flowable inert carrier and the mixture can be directly tableted, without passing the granulation or slug formation step mentioned above. A transparent or semitransparent protective coat composed of a tight shellac layer, or a sugar or macromolecular material coat, and a polish coat composed of a wax can also be used.

Other oral dosage forms, for example syrups, elixirs and suspensions, can also be prepared in unit dosage forms so that a certain specific amount thereof contains a certain specified amount of the active ingredient. Syrups are produced by dissolving the active ingredient in an appropriate aqueous flavoring solution, while elixirs are produced by using a nontoxic alcoholic carrier. Suspensions are prepared by dispersing the active ingredient in a nontoxic carrier. Suspending agents or emulsifiers (e.g. ethoxylated isostearyl alcohol, polyoxyethylenesorbitol esters), preservatives, flavorings (e.g. peppermint oil, saccharin) and other additives may optionally be added.

When necessary, the unit dosage formulations for oral administration may be microencapsulated. Said formulations can also be converted to long-acting or sustained release formulations by coating or by embedding the active ingredient in a macromolecular substance, a wax or the like.

Subcutaneous, intramuscular, intraarterial or intravenous administration can be realized by preparing a liquid unit dosage form, for example an injection in solution or suspension form. These forms are produced by dissolving or suspending a certain amount of the active ingredient in a nontoxic liquid carrier suited for the purpose of injection, for example an aqueous or oleaginous solvent and then sterilizing the solution or suspension. The active ingredient may be pulverized or lyophilized and then distributed in certain specific portions into vials, followed by sterilization of the vials and vial contents and tight closing. In this case, reserve vials or carriers may be prepared for dissolution or reconstitution just prior to use.

A nontoxic salt or salt solution may be added for isotonizing the injections. A stabilizer, a preservative, a suspending agent and/or an emulsifier can further be added.

Dosage forms for rectal administration can be prepared by kneading the active ingredient with a hydrophobic or hydrophilic suppository base, for example polyethylene glycol, cacao butter, a higher ester (e.g. myristyl palmitate), a glyceride (hard fat), or a mixture of these.

Administration of DHEA-S.Na to patients with MyD in accordance with the present invention can result in increases in blood DHEA and DHEA-S levels and in a marked improvement with respect to the phenomenon of myotonia in patients with MyD and in an improvement in activity of daily living (hereinafter briefly referred to as ADL).

The improved efficacy of the remedy for myotonic dystrophy according to the present invention on the phenomenon of myotonia and on the ADL can last even one to two months after the end of the DHEA-S administration period.

The remedy for myotonic dystrophy according to the present invention can be safely used since it never produces such an adverse effect as masculinization due to male hormonal actions in female patients.

Administration, according to the present invention, of DHEA-S.Na to patients with MyD can result in improvements in ADL mainly relating to muscles of the neck, intrinsic muscles of the back and proximal muscles of the limbs, namely improvements in ADL relative to head raising from the decubitus, walking, going up and down the stairs, standing up and so on. Manual muscle testing has established that the administration of DHEA-S.Na to patients with MyD in accordance with the present invention can increase the power of said muscles.

No conventional remedies have ever produced such effects.

In cases in which the conventional drugs had failed to produce symptomatic improvements and in which DHEA-S.Na was administered according to the present invention, it was confirmed that the administration of DHEA-S.Na led to substantial disappearance of myotonia. By this, it was established that the remedy for myotonic dystrophy according to the present invention is markedly efficacious as compared with the prior art remedies.

In connection with the above effects, the time course of muscular response findings upon repeated nerve stimulation as obtained from electromyography revealed a rise of the threshold of the manifestation of the myotonia phenomenon.

Although the reason why the administration of DHEA-S.Na produces such efficacies is not yet certain, it is presumable that it should act on the muscle cell membrane of patients with MyD, increasing the stability of said cell membrane.

While it is not certain whether the efficacy of the remedy for myotonic dystrophy according to the present invention is directly attributable to DHEA-S or to the in vivo conversion product DHEA, it is presumable that DHEA-S.Na administered is retained in blood as DHEA-S and, as necessity requires, gradually converted to DHEA, which is thought to be the active form, thus producing long-lasting efficacy, since the half-life of DHEA-S in blood is as long as 7 to 11 hours and that of DHEA is as short as 15 minutes.

Since the efficacy and utility of the present invention have thus been established in patients with MyD, said remedy is presumably efficacious also in the treatment of muscular dystrophy, which is likewise caused by abnormalities in the muscle cell membrane, and other myotonia diseases showing myotonia as a symptom.

BEST MODES FOR CARRYING OUT THE INVENTION

The following examples are further illustrative of the present invention but are by no means limitative of the scope thereof.

Example 1 Preparation for injection

With informed consent, three patients with MyD (one male and two females, average age 42), who had been refractory to the conventional drug therapies, were subjected to therapy with DHEA-S.Na. In all the cases, no physical therapy was given.

During the 10 day placebo period, physiological saline was given by intravenous injection and no subjective and objective changes were noted. Thereafter, a solution of 200 mg of DHEA-S.Na in distilled water for injection was intravenously administered once daily for consecutive 8 weeks.

On the 8th day or so of administration, the effect manifested itself, developing a tendency toward gradual improvement. Toward the end of the administration period, the phenomenon of myotonia had nearly disappeared and improvements of ADL and slight increases in muscular strength were observed. This effect was found lasting even one to two months after the end of the administration period. Throughout the whole course, no adverse effects were noted.

Example 2 Preparation for oral administration

Two patients with MyD (one male and one female, average age 38) were orally given a capsule containing 100 mg of DHEA-S.Na twice (morning and evening) daily for consecutive 12 weeks. They were given no physical therapy during the period of administration. Substantially the same results as in Example 1 were obtained by this oral administration, too.

Dosage Form Example 1 (Production of capsules)

(Formulation)

| Ingredient | Amount (g) |
| --- | --- |
| DHEA-S.Na (dihydrate) | 546 |
| Mannitol | 144 |
| Magnesium stearate | 10 |

(Procedure)

The above ingredients were homogeneously mixed up and distributed in 140 mg portions into capsules to give capsules each containing 100 mg of DHEA-S.Na (on the anhydrous basis).

Dosage Form Example 2 (Production of tablets)

(Formulation)

| Ingredient | Amount (g) |
| --- | --- |
| DHEA-S.Na (dihydrate) | 109 |
| Lactose | 60 |
| Corn starch | 28 |
| Hydroxypropylcellulose | 2 |
| Magnesium stearate | 1 |

(Procedure)

DHEA-S.Na (dihydrate), lactose and corn starch were homogeneously mixed up and the mixture was passed through a 60 mesh sieve. An aqueous solution of hydroxypropylcellulose was added to the sieved mixture, followed by kneading, granulation and drying. Then, magnesium stearate was added and the whole mixture was tableted to give tablets each weighing 200 mg. Thus, tablets each containing 100 mg of DHEA-S.Na (on the anhydrous basis) were obtained.

Dosage Form Example 3 (Production of an injection)

(Formulation)

| Ingredient | Amount (g) |
| --- | --- |
| DHEA-S.Na (dihydrate) | 44 |
| Glycine (stabilizer) | 40 |

(Procedure)

Purified water was added to glycine for dissolution of the latter. Thereto was added DHEA-S.Na (dihydrate) with warming to cause dissolution of the same. Then, the whole amount was made 2,000 ml. The resultant solution was sterilized by filtration and then distributed in 5 ml portions into receptacles for injection (vials), followed by lyophilization. Thus was obtained an injectable preparation to be extemporaneously dissolved, each vial containing 100 mg of DHEA-S.Na (on the anhydrous basis).

Dosage Form Example 4 (Production of an injection)

(Formulation)

| Ingredient | Amount (g) |
| --- | --- |
| DHEA-S.Na (dihydrate) | 44 |
| Glycine (stabilizer) | 40 |

(Procedure)

Purified water was added to glycine for dissolution of the latter. Thereto was added DHEA-S.Na with warming to cause dissolution of the same. Then, the whole amount was made 2,000 ml. The resultant solution was sterilized by filtration and then distributed in 10 ml portions into receptacles for injection (vials), followed by lyophilization.

Thus was obtained an injectable preparation to be extemporaneously dissolved, each vial containing 200 mg of DHEA-S.Na (on the anhydrous basis).

| Dosage Form Example 5 (Production of suppositories) | |
| --- | --- |
| (Formulation) | |
| Ingredient | Amount (g) |
| DHEA-S.Na (dihydrate) | 44 |
| Hard fat (Witepsol H-15, product of Dynamit Nobel) | 266 |
| Glycine (stabilizer/ absorption enhancer) | 10 |
| (Procedure) | |

The hard fat was placed in a stainless steel beaker and melted by warming at 40° to 42° C. Thereto were added DHEA-S.Na (dihydrate) and glycine, and the mixture was stirred until it became homogeneous. This mixture, while maintained at 37° to 38° C., was casted in 1.6 g portions into spindle-shaped molds and then cooled to give suppositories each containing 200 mg of DHEA-S.Na (on the anhydrous basis).

INDUSTRIAL APPLICABILITY

By administering DHEA-S.Na as a remedy for myotonic dystrophy to patients with MyD in accordance with the present invention, a much more marked efficacy can be produced on the improvement of myotonia and ADL as compared with the prior art remedies.

We claim:

1. A method for treating a patient suffering from myotonic dystrophy comprising administering to said patient a pharmaceutical preparation containing dehydroepiandrosterone sulfate or a pharmacologically acceptable salt thereof in an amount effective for treating myotonic dystrophy.

2. The method according to claim 1 wherein the dosage form of said preparation is an injectable preparation.

3. The method according to claim 1 wherein the dosage form of said preparation is a preparation for oral administration.

4. The method according to claim 3 wherein the dosage is 10 to 2,000 mg/day.

5. The method according to claim 3 wherein the dosage is 50 to 1000 mg/day.

6. The method according to claim 1 wherein the pharmacologically acceptable salt of dehydroepiandrosterone sulfate is the sodium salt of dehydroepiandrosterone sulfate.

7. The method according to claim 1 which comprises parenteral administration using a dosage of 10 to 1000 mg/day.

8. The method according to claim 1 which comprises parenteral administration using a dosage of 50 to 500 mg/day.

9. A method for treating a patient suffering from a condition of myotonic dystrophy or from the phenomenon of myotonia in a disease manifesting myotonia comprises administering to said patient a pharmaceutical preparation containing dehydroepiandrosterone sulfate or a pharmacologically acceptable salt thereof in an amount effective for treating said condition.

10. The method according to claim 9, wherein the dosage form of said preparation is an injectable preparation.

11. The method according to claim 9, wherein the dosage form of said preparation is a preparation for oral administration.

12. The method according to claim 11, wherein the dosage is 10 to 2,000 mg/day.

13. The method according to claim 11, wherein the dosage is 50 to 1,000 mg/day.

14. The method according to claim 9, wherein the pharmacologically acceptable salt of dehydroepiandrosterone sulfate is the sodium salt of dehydroepiandrosterone sulfate.

15. The method according to claim 9, which comprises parenteral administration using a dosage of 10 to 1,000 mg/day.

16. The method according to claim 9, which comprises parenteral administration using a dosage of 50 to 500 mg/day.

* * * * *